United States Patent [19]

Strand

[11] Patent Number: 5,219,566
[45] Date of Patent: Jun. 15, 1993

[54] IMMUNOPROPHYLACTIC POLYPEPTIDES FOR SCHISTOSOMIASIS

[75] Inventor: Mette Strand, Baltimore, Md.

[73] Assignee: The Johns Hopkins University, Baltimore, Md.

[21] Appl. No.: 725,804

[22] Filed: Jul. 9, 1991

Related U.S. Application Data

[63] Continuation-in-part of Ser. No. 252,075, Sep. 30, 1988, Pat. No. 5,051,254.

[51] Int. Cl.[5] .................. A61K 39/00; C12N 15/11
[52] U.S. Cl. ......................... 424/88; 530/350; 530/395; 435/69.3; 536/23.5
[58] Field of Search .............. 536/27; 424/88; 435/69.3, 69.7; 530/350, 395

[56] References Cited

PUBLICATIONS

Strand (1987) J. Cell. Biochem Suppl 11A, 152.
Sher et al. (1982) J. Immunol. 128 (4), 1880–1884.
Morein et al (1984) Nature 308, 457–460.
Grzych, Nature, vol. 316. pp. 74–76, 1985.
Capron, Molecular Paradigms for the Eradication of Helminthic Parasites, J. Cell, Biochem., Suppl. 11A, 1987, p. 151, Abstract C024.
Oligino, Molecular Paradigms for the Eradication of Helminthic Parasites J. Cell, Biochem., Suppl. 11A, 1987, p. 151, Abstract C025.
Dissous, Molec. and Biochem., Parasitology, vol. 16, pp. 277–288, (1985).
Kelly, Parasite Immunology, vol. 8, pp. 193–198.
Smithers, Acta Tropica, vol. 44, Suppl. 12, pp. 21–30, (1987).
Lanar, Science, vol. 234, pp. 593–596, (1986).
Newport, Molec. and Biochem. Parasitology, vol. 26, pp. 29–38, (1987).
Second Conference on the Molecular Biology of Schistosomes.
Dalton, J. Immunolgy, vol. 139, pp. 2474–2481 (1987).
Dalton, Experimental Parasitology, vol. 63, pp. 215–226, (1987).
Tom, "Cloning of cDNAs Encoding Schistosomula Antigens," in Molecular Paradigms for Eradicating Helminthic Parasites, A. J. MacInnis, ed., pp. 105–118, Alan R. Liss, N.Y. (1987).

*Primary Examiner*—Robert A. Wax
*Assistant Examiner*—R. Keith Baker
*Attorney, Agent, or Firm*—Banner, Birch, McKie & Beckett

[57] ABSTRACT

Polypeptide epitopes are defined herein which when used as components of vaccine compositions, induced partial immunity to *Schistosoma mansoni*. The epitopes are found on the surface of schistosumula. The epitopes are part of larger proteins which are immunologically cross-reactive with myosin heavy chains from other species. However, anti-myosin antibodies directed against myosin molecules of other species are not cross-reactive with the surface epitopes of *S. mansoni*.

6 Claims, 4 Drawing Sheets

FIG. 1A

```
   1 GAATTCAAAC AACGTTACTC GATTTTGGCA CCAAATGTTA TACCTGATGG
  51 ATTTGTTGAT GGTCGTCAAG TTACAGAAAA AATATTGGAA GCAACACAAT
 101 TAGATAAAAA TCTTTATCAA TGCGGTAATA CAAAAGTATT TTTCAAAGCT
 151 GGCACCCTAG CTCATTTAGA AGATTTACGT GATGATAAAT TAAATGGTAT
 201 TATTAGTTTA TTCCAAGCAG AAATTCGTGG TTATTTAATG AGAAAACAAT
 251 ATAAAAAGCT ACAAGATCAA CGTGTTGCAC TTACATTAAT GCAACGTAAT
 301 ATACGTAAAT ATTTAGTATT ACGTAATTGG CCATGGTGGA GATTATATAC
 351 AAAAGTGAAA CCAATGTTAA ATATAGCACG TCAAGAAGAA GAAATGAAAA
 401 AAGCCGCTGA AGAATTAGCC AAATTAAAAG AAGAATATGA AAAATTAGAA
 451 AAATTAAAAA AAGAATTAGA AGAACAAAAT GTCACTGTAT TACAACAAAA
 501 AAATGATTTA TTTTTACAAT TACAAACTGA ACAAGATAGT TTAGCTGATG
 551 CTGAAGAGAA AATTACCAAG CTTGTGCTAC AACGTGGTGA TATGGAACAA
 601 CGTATTAAAG AATTAGAAGA ACGTTTAGCT GATGAAGAAG ATCAAGCAGC
 651 TAATCTGACT GAAGTGAAAA AGAAAATGTC CGCTGAAATT GAAGAATTAA
 701 AAAAAGATGT TGAAGATTTA GAATCATCAT TACAAAAAGC TGAACAAGAA
 751 AAACAAACTA AAGATAATGA AATACGTACA TTACAATCAG AAATGGCACA
 801 ACAAGATGAA ATGATTGGAA AATTAAATAA AGATAAAAAA AATTTAGAAG
 851 AAGAAAATAA ACGTACACAA GAAGCATTAC AAGCTGAAGA AGATAAAGTG
 901 AATCATTTGA ATAAATTAAA AGCTAAATTA GAATCAACAT TAGATGAAAT
 951 GGAAGAAAAT CTAGCTCGTG AACAAAAGAT TCGTGGTGAT GTAGAAAAAT
1001 CTAAACGTAA ATTAGAAGGT GATTTAAAAG CTACACAAGA AACTGTTGAT
1051 GATTTGGAAC GTGTAAAACG TGACTTAGAA GAACAATTAC GACGTAAAGA
1101 AGCTGAAATT GGTGGTTTAA GTGGGAAATT TGAAGATGAA CAAGGTTTAG
1151 TAGCACAGTT ACAACGAAAA ATTAAAGAAC TTCAAACACG TATACAAGAA
1201 TTAGAAGAAG ATTTAGAAGC GGAACGTGCA GCTCGTTCAA AAGCTGAAAA
1251 GAGTCGACAA CAACTTGAAA GTGAATTAGA AGAAGTTGTT GATCGTTTAG
1301 AAGAACAAGA TGGTGCTACA GCAGCACAAA GTGATTTAAC TAAAAAACGT
1351 GAAGCTGAAT TAATGAAATT AAAACGTGAT TTAGAAGATA CACGTTTACA
1401 AAATGAACAA GCTATAGCTA CAATGCGTAA AAAACAAAGT GATGCTATTA
1451 ATGAATTAGC TGATCAATTA GATCAAGCTA ATAAAGCTAA AGCAAAAGCT
1501 GAAAAAGAAC GAAGTCAATT CAAAGCTGAA TTAGATGATG CACATAATCA
1551 GGTGGATAGT ATTATGAAAG CTAAATTGAA TTC
```

```
I.    1'    EFKQRYSILAP---NVIPD--GFVDGRQVTEKILEATQLDKNLYQCGNTKVFFKAGTLAH
            : ::: :::        :    :           : ::   :::::::  ::::::::: :::
            :: :::::::::     :  :    : :: ::::::: ::::::: :::::::::: :::
II.   727'  DFVQRYAILAAKEAKSDDD--KKKCAEAIMSKLVNDGSLSEEMFRIGLTKVFFKAGVLAH

I.    56'   LEDLRDDKLNGIISLFQAEIRGYLMRKQYKKLQDQRVALTLMQRNIRKYLVLRNWPWWRL
            ::: ::  :    : ::  ::   :   :    :: :    ::: :    :: :   :
            :::::::::::::: ::::: ::  :: :::::: :::::: :::::::::: :::: ::::
II.   785'  LEDIRDEKLATILTGFQSQIRWHLGLKDRKRRMEQRAGLLIVQRNVRSWCTLRTWEWFKL

I.    116'  YTKVKPMLNIARQEEEMKKAAEELAKLKEEYEKLEKLKKELEEQNVTVLQQKNDLFLQLQ
            : :::::: ::      ::   :     :     :   :::  :::::     :  ::  :
            ::::::::::  :::::::: ::::   :::: ::  :::::::::  ::::::::::: :::
II.   845'  YGKVKPMLKAGKEAEELEKINDKVKALEDSLAKEEKLRKELEESSAKLVEEKTSLFTNLE

I.    176'  TEQDSLADAEEKITKLVLQRGDMEQRIKELEERLADEEDQAANLTEVKKKMSAEIEELKK
              : ::::   ::  :  :     ::   :: :::::::::    :::  :: : :::
            :::: :::::::::::: :: : ::::::::::::::::::         :::::::::::::
II.   905'  STKTQLSDAEERLAKLEAQQKDASKQLSELNDQLADNEDRTADVQRAKKKIEAEVEALKK

I.    236'  DVEDLESSLQKAEQEKQTKDNEIRTLQSEMAQQDEMIGKLNKDKKNLEEENKRTQEALQA
            ::: ::  ::: :::  :: ::  :: :: :::: :  :  :  : :   :  :    :::
            :::::: ::::::::::::::::::::::::::::::::::: :: ::: ::::::
II.   965'  QIQDLEMSLRKAESEKQSKDHQIRSLQDEMQQQDEAIAKLNKEKKHQEEINRKLMEDLQS

I.    296'  EEDKVMHLNKLKAKLESTLDEMEENLAREQKIRGDVEKSKRKLEGDLKATQETVDDLERV
            :::: :  :::::  :::::: : ::    : : :: : : : ::::::: :  ::::::::
            ::::: :::::::::::::: ::::::::::::::::: :::::: : ::::::::::::::::
II.   1025' EEDKGNHQNKVKAKLEQTLDDLEDSLEREKRARADLDKQKRKVEGELKIAQENIDESGRQ

I.    356'  KRDLEEQLRRKEAEIGGLSGKFEDEQGLVAQLQRKIKELQTRIQELEEDLEAERAARSKA
            : :   :    :::: ::  :::  :  : :: :::: :: :::::::::::  ::::
            :::::::::::::::::::::::::::::::::  ::::: ::::::::::::::::::::::
II.   1085' RHDLENNLKKKESELHSVSSRLEDEQALVSKLQRQIKDGQSRISELEEELENERQSRSKA

I.    416'  EKSRQQLESELEEVVDRLEEQDGATAAQSDLTKKREAELMKLKRDLEDTRLQNEQAIATM
             :  :::::  : ::    :  ::::::  ::::::: ::::  :::   :
            ::::::::::::::::::::::::::::::::::::::::::::::::::::::::::::::
II.   1145' DRAKSDLQRELEELGEKLDEQGGATAAQVEVNKKREAELAKLRRDLEEANMNHENQLGGL

I.    476'  RKKQSDAINELADQLDQANKAKLKAEKERSQFKAELDDAHNQVDSIMKAKLN
            :::  :: ::: ::::::: : ::::::   : :  :::::::::  :
            :::::::::::::::::::::::::::::::::::::::::::::::::
II.   1205' RKKHTDAVAELTDQLDQLNKAKAKVEKDKAQAVRDAEDLAAQLDQETSGKLN
```

IMMUNOPROPHYLACTIC POLYPEPTIDES FOR SCHISTOSOMIASIS

The work leading to this invention was supported in part by grants from the National Institutes of Health. The U.S. government retains some rights in the invention.

This application is a continuation-in-part of U.S. Ser. No. 252,075, filed Sep. 30, 1988, now U.S. Pat. No. 5,051,254.

FIELD OF THE INVENTION

The present invention relates to prophylaxis against *Schistosoma mansoni*, which causes big belly disease or biharziasis.

BACKGROUND OF THE INVENTION

Schistosomiasis is a parasitic infection of man which is wide-spread in tropical countries. Schistosomiasis, known as biharziasis in Europe and as big belly disease in China, ranks as one of the most debilitating of tropical infections. Schistosomiasis is the result of infection with sexually mature and reproducing adult worms of any one of several closely related species of parasitic flat worms. The disease occurs where the parasite's specific small intermediate hosts are found. Approximately 250 million people are estimated to be infected, with about 5% of those displaying severe disease symptoms.

Human schistosomiasis is transmitted by water contact. The cercariae, or mobile larvae, emerge from the snail host and penetrate the skin of humans, where they rapidly develop into schistosomula. The schistosomula enter the blood stream and migrate to the lungs at 4 to 14 days. The schistosomula re-enter the blood stream migrating to the mesenteric or pelvis venules where they mate and lay eggs.

Often, upon infection, a rash occurs at the penetration site. Other symptoms include cough, fever, eosinophilia, and asthma-like symptoms. The adult worm grows to approximately 1.5 cm and can lay up to 500 eggs a day.

While there are some drugs which effectively counter infection, drug resistance as well as incomplete curing of worms creates recurrence problems. Effective vaccines are needed to provide lasting protection from these infections in areas of the world where water sources will continue to remain contaminated with fecal matter.

OBJECTS OF THE INVENTIONS

It is an object of the invention to provide a fusion protein which can stimulate an immune response resulting in protective anti-bodies which recognize surface antigens of schistosomula.

It is another object of the invention to provide antibodies which bind to epitopes expressed on the surface of live schistosomula.

It is yet another object of the invention to provide polypeptides which are capable of binding to antibodies which bind to antigens on the surface of live schistosomula.

It is still another object of the invention to provide vaccines comprising polypeptides which bind to antibodies which bind to the surface of live schistosomula, in combination with an immune adjuvant. These and other objects of the invention are provided by one or more of the embodiments described below.

In one embodiment a preparation is provided comprising antibodies which bind to protein epitopes expressed on the surface of live schistosomula of *S. mansoni*. The protein epitopes are common to two glycopropteins of *S. mansoni*, of sizes 200 kDa and 38 kDa, but are not immunologically cross-reactive with antibodies raised against bovine or *C. elegans* myosin.

In another embodiment of the present invention a fusion protein is provided which, when injected into mice to stimulate an immune response, elicits production of antibodies which recognize protein epitopes expressed on the surface of live schistosomula of *S. mansoni*, said protein epitopes being common to a 200 kDa and a 38 kDa glycoprotein of *S. mansoni*; said protein epitopes are not immunologically cross-reactive with antisera raised against bovine or *C. elegans* myosin.

Figure 1A:
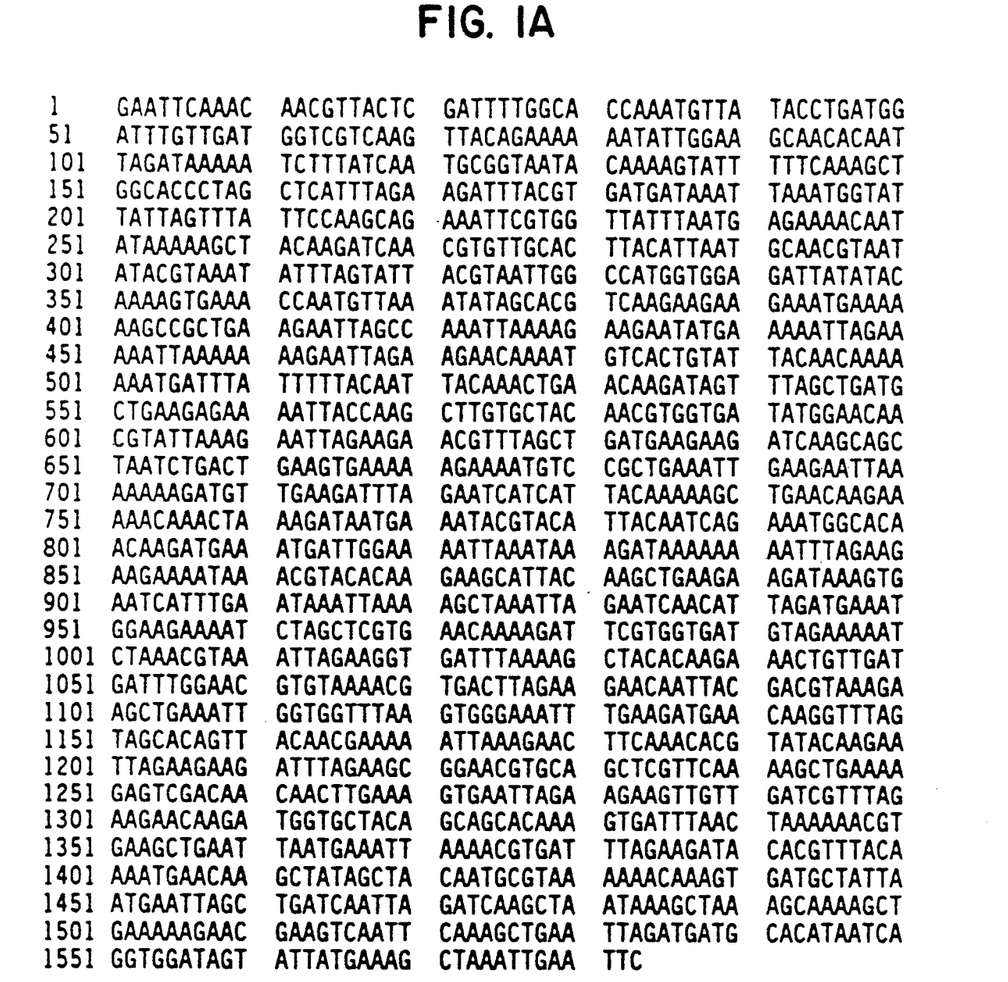
Figure 1C:
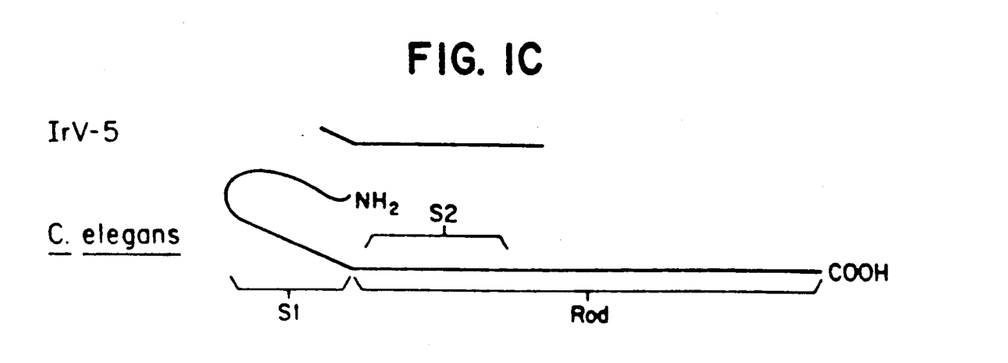

In another embodiment of the present invention polypeptides are provided which bind to the antibodies which bind to protein epitopes expressed of the surface of *S. mansoni* schistosomula. The polypeptides have a sequence corresponding to that shown in FIG. 1. The polypeptide can be synthesized chemically, or can be synthesized by a transformed host cell carrying a recombinant DNA sequence which codes for the polypeptide. Vaccines are also provided by the present invention which comprises either the polypeptide or the fusion protein of the present invention in combination with an immune adjuvant.

The present invention provides means of generating large quantities of protein antigens. The antigens can be synthesized either chemically or by recombinant DNA techniques to provide large quantities of immunogens for vaccine production and testing.

BRIEF DESCRIPTION OF THE FIGURES

FIGS. 1A-C: panel A depicts the nucleotide sequence of the insert of clone IrV-5. Panel B shows the deduced amino acid sequence of clone IrV-5 insert DNA in line I, and the myosin heavy chain of *C. elegans* amino acid sequence in line II. Panel C shows a diagrammatic illustration of the region of homology between the deduced amino acid sequence of clone IrV-5 and *C. elegans* myosin heavy chain.

DETAILED DESCRIPTION OF THE INVENTION

It has been discovered that epitopes which are common to two glycoproteins (38 kDa and 200 kDa) of schistosomula of *S. mansoni* are able to provide protection against infection by *S. mansoni*. The epitope (or epitopes) on the 38 kDa protein are exposed to the surface of the schistosomula. The epitope on the 200 kDa protein is apparently not exposed to the surface of schistosomula.

The 38 kDa protein is immunologically cross-reactive with antisera to both bovine smooth uterine muscle myosin as well as *C. elegans* myosin. However, the particular epitopes of the present invention which are shared by the 200 and 38 kDa proteins and which are exposed to the surface of schistosomula, are not immunologically cross-reactive with the anti-myosin antisera of cows or *C. elegans*. In addition, other previously known antibodies which are cross-reactive with the 38 kDa glycoprotein, such as monoclonal antibody 128 (Dalton, et al., Experimental Parasitology, vol. 63, pp. 215-226, 1987) are not immunologically cross-reactive with the epitopes identified by the present invention. Previously described antibodies which recognize surface epitopes on the 38 kDa glycoprotein are directed against glycanic moieties. One benefit of the epitopes identified by the present invention (as compared to the previously identified glycanic epitopes) is that the protein epitopes can be synthesized by means of organisms containing recombinant DNA.

The proteinaceous character of the epitopes identified in the present invention is evident from the following fact: the epitopes are identified by antisera which were raised against lysates of bacteria infected with recombinant phage. As bacteria do not glycosylate proteins, the epitopes must be protein epitopes rather than glycanic epitopes.

A fusion protein according to the present invention may include portions of any bacterial protein which is well expressed. Particularly convenient fusion proteins are made using portions of the amino terminal end of the enzyme beta-galactosidase. Other bacterial proteins are known in the art and may be used to obtain expression in bacteria. If expression in other types of host cells is desired, fusions may be made to proteins of the host cell which are conveniently expressed. In the course of constructing the particular fusion protein which is exemplified below, a lambda gt11 vector was used to create the fusion protein. *S. mansoni* cDNA was inserted into the lambda gt11 DNA in order to create a library of *S. mansoni* genes. A description of the making of the cDNA library can be found in the Proceedings of the National Academy of Sciences U.S.A., vol. 84, page 4268, 1987. Techniques for making cDNA libraries are well known in the art. See, e.g., Maniatis et al., *Molecular Cloning*, pp. 211-246, Cold Spring Harbor Laboratory, 1982.

The clones of the present invention which contain the protein epitopes common to both the 200 kDa and the 38 kDa glycoprotein were identified using a rabbit antiserum (termed anti-IrV) which was raised against a subset of adult worm antigens, including the 200 kDa glycoprotein. The particular subset of adult worm antigens was selected based on its enhanced reactivity with sera of vaccinated as compared to chronically infected mice. The subset of antigens were purified using immunoprecipitation and immunodepletion techniques. See, Dalton et al., J. Immunology, vol. 139, pp. 2474-2481, 1987. Five clones were identified out of 20,000 plaques screened which reacted immunologically with the anti-IrV serum.

One clone, identified as IrV-5, contains *S. mansoni* sequences which share 48% identity with the amino acid sequence of the heavy chain of *C. elegans* myosin. However, the identity is located in a region of the sequence distinct from that region which contains the protein epitopes shared by the 200 kDa and the 38 kDa glycoproteins of *S. mansoni*. Thus the epitopes identified in the present invention are not cross-reactive with anti-myosin antisera directed against either bovine or *C. elegans* myosin.

Polyclonal antibodies against bovine uterine smooth muscle myosin and a monoclonal antibody (12.1.1) against the S2 region of myosin heavy chain of *C. elegans* immunoreact with the fusion polypeptide. However, the anti-bovine and anti-*C. elegans* antibodies do not immunoreact with surface epitopes of schistosomula. In contrast, antisera raised against the native fusion protein encoded by clone IrV-5, are able to specifically immunoprecipitate a 38 kDa component from an extract of radio-iodinated, surface labeled schistosomula. Thus, anti-schistosome myosin antibodies define epitopes exposed on the surface of live schistosomula, and these epitopes are not recognized by antibodies against myosin derived from other species.

A fusion protein, according to the present invention, can be synthesized in any heterologous host cell. As is known in the art, vectors for particular host cells are available and can be used to maximize protein production. Suitable host cells include yeast cells, *E. coli* cells, and other readily culturable cells.

Surface expression of the epitopes of the present invention can be detected using indirect immunofluorescence analysis. Surface integrity of schistosomula during the course of the immunofluorescence assays can be verified using diamindinophenylindole, a fluorochrome specifically taken up by damaged schistosomula. Antibodies raised against the fusion protein of the present invention as well as monoclonal antibody 128 show strong binding to the surface of live newly transformed schistosomula.

Surface binding can be detected in the following way. Live schistosomula can be incubated for about one hour on ice with the test antibody. Antibody which binds to the surface of the schistosomula can be detected using antibody raised against immunoglobulin of the species of the first antibody. Rhodamine-conjugated protein A can be used to identify the bound antibodies. Alternatively, the anti-immunoglobulin antibody can itself be conjugated to a fluor such as fluorescein isothiocyanate. The schistosomula are washed three times after each antibody incubation. Immunofluorescence using frozen sections can be carried out as described in The Journal of Immunology, vol. 137, page 3593, 1986. Other means of detecting surface binding are known in the art and can be used as is convenient.

An alternative method for identifying surface epitopes is to radio-iodinate surface polypeptides. Surface labeling can be accomplished using the Iodo-Gen method described in The Journal of Immunology, vol. 139, page 2474, 1987. The surface labeled proteins can be extracted with a detergent for example 1% NP 40, and immunoprecipitated, as described in The Journal of Immunology, vol. 136, page 4689, 1986. The extracted proteins can be separated on polyacrylamide gels by means of electrophoresis, and identified immunologically be means of immunoblotting.

Antibody to be used for testing polypeptides to determine whether they contain the protein epitopes according to the present invention include those directed against bovine smooth uterine muscle myosin, which can be obtained from ICN ImmunoBiologicals, Lisle, Ill. Antibody directed against myosin of *C. elegans* is described in Miller et al., Proceeding of the National Academy of Sciences U.S.A., vol. 83, page 2305, 1986.

The polypeptides of the present invention can be synthesized chemically according to methods which are well known in the art. The polypeptide need not contain all of the amino acids shown in FIG. 1, as many may be unnecessary for the epitope structure claimed herein. Polypeptides can be synthesized according to the Merrifield solid phase procedure, which is well known in the art. Alternatively the polypeptide can be synthesized in a recombinant DNA containing organism, as described above. It is most convenient to synthesize the polypeptide of the present invention as a fusion protein. The critical characteristic of the polypeptides of the present invention is that they are able to bind to the antibodies which are immunoreactive with protein epitopes expressed on the surface of live schistosomula of S. mansoni. The surface epitopes bound by the antibodies are common to both the 200 kDa and the 38 kDa glycoproteins, and these epitopes are not immunoreactive with antibodies directed against bovine or C. elegans myosin.

Vaccines according to the present invention are composed of the polypeptide which contains the protein epitopes shared by the 200 kDa and the 38 kDa proteins and an immune adjuvant. The adjuvant can be any which is known in the art of immunization. These include C. parvum, and Freund's adjuvant. A particularly preferred vaccine contains the polypeptide complexed to Quil A (saponin extract from Quillajabark Araloside A) produced according to K. Dalsgaard, Saponin Adjuvants III, Archiv fur die Gesamte Virus Forschung, vol. 44, pp. 243-254, 1974, which has been centrifuged to form iscoms, as described in Morein et al., Nature, vol. 308, page 457, 1984. Another desirable vaccine formulation comprises multimeric protein preparations (proteosomes). See Ruegg et al., J. Imm. Methods, vol. 135, pp. 101-109, 1990. Briefly, an immunogenic polypeptide is derivatized at the N-terminus by a lipopeptide moiety, e.g., lauroyl-Cys-Tyr-Gly-Gly. The derivatized polypeptide is mixed with menigococcal outer membrane proteins (OMP) to a final OMP concentration of 1 mg/ml and dialyzed for about 7-10 days. OMP from Group B Neissera meningitidis has been found to be suitable for this use. Preferably the proteosomes will have a ratio of polypeptide of the present invention to outer membrane proteins (OMP) of about 2:1 (w/w). The dosage of antigen given for immunizations will generally be between about 10 μg and 1 mg. The vaccines can be administered in any physiologically acceptable diluent.

The DNA preparations according to the present invention are any which when transcribed and translated, in vitro or in vivo, to yield a sequence as shown in FIG. 1, panel B, line I. As is understood, it is only necessary that the regions of the sequence necessary to form the protein epitopes which are common to the 200 kDa and the 38 kDa proteins be present. It is not necessary that the exact coding sequence of DNA isolated from schistosomula be present, but only those sequences which lead to the same amino acid sequence or functionally equivalent amino acid sequences which are able to bind to the antibodies of the present invention.

EXAMPLE 1

This example demonstrates the purification of antigens which are specific to vaccinated mice by sequential immunoaffinity chromatography. In addition, the use of these antigens to make a polyclonal antiserum is demonstrated.

Immunodepletion permitted identification of a subset of schistosomula and adult worm glycoproteins that can be defined as "vaccine-specific." These vaccine-specific antigens from adult worms were purified using preparative sequential immunochromatography. The resulting glycoproteins constitute only a very minor fraction of the total proteins. These glycoproteins were used to immunize and raise antiserum in a rabbit. This antiserum is termed anti-IrV, which stands for anti-irradiated-vaccinated serum. Schistosomula and adult worm glycoproteins metabolically labeled with $^{35}$S-methionine were first immunodepleted with sera from patently infected mice before immunoprecipitation with sera from vaccinated mice. All of the antigens detected by this technique bound to concanavalin A and are therefore glycosylated.

Immunoprecipitations were carried out as described in Norden et al., Experimental Parasitology, vol. 58, page 333, 1984 and vol. 57, page 110, 1984. Sequential immunoprecipitations were carried out using serum from patently infected and once or twice vaccinated mice. Immunodepletion with antiserum from patently infected mice was performed as follows: 50,000 dpm of methionine-labeled schistosomula or adult worm polypeptide preparations were incubated for 18 hours with 2 ul of serum from patently infected mice. To assure precipitation of all classes and isotopes of Ig, 10 ul of affinity-purified rabbit IgG reactive with mice IgG, IgM, IgA, and IgD (Jackson Immuno Research Laboratories, Inc., Avondale, Pa.) were then added. After a further four hour incubation, immune complexes were precipitated with 5 ul of a 50% suspension of Staphlococcus aureus. The supernatant was collected and the precipitation reaction repeated twice with the same antiserum (from patently infected mice). The final supernatant was transferred to a fresh tube and then precipitated with 2 ul of the other antiserum. Reciprocal immunodepletion experiments in which incubation with antiserum from one or twice vaccinated mice was followed by precipitation with antiserum from patently infected mice were carried out in the same manner.

IgG molecules capable of binding to staphylococcal protein A were isolated from sera of normal, patently infected, and vaccinated mice using protein A-Sepharaose CL-4B (Pharmacia Fine Chemicals, Piscataway, N.J.). These purified mice IgGs were then separately coupled to cyanogen bromide-activated Sepharose 4B (Pharmacia) following the manufacturer's instructions. Approximately 10 mg of S. mansoni adult worm concanavalin A-binding glycoproteins, isolated as described above, were applied to the normal mouse IgG affinity column. The unbound fraction was then applied and recycled six times over an immunoaffinity column prepared with IgG from patently infected mice. The antigens that did not bind to these two columns were applied and recycled six times over a third immunoaffinity column prepared with IgG from sera of mice vaccinated twice with irradiated cercariae. This column was then washed extensively with 20 mM tris(-hydroxymethyl)aminomethane-HCl, pH 8.0, containing 1 mM ETA, 0.1M sodium chloride, 2.5M potassium chloride and 0.1% N octyl-beta-D-glucopyranoside (washing buffer) and the bound antigens were eluted with 0.05M diethylamine, pH 11.5. The eluted fractions were immediately neutralized with 1M sodium bicarbonate, pH 8.0, and dialyzed and concentrated against phosphate-buffered saline, pH 7.3, containing 0.1% N-octyl-beta-D glucopyranoside.

A New Zealand white rabbit was immunized with approximately 1 μg of immunoaffinity-purified antigens at two subcutaneous sites every three weeks for a total of four immunizations. Muramyl dipeptide-threonine, provided by Dr. A. Allison (Syntex Laboratories, Inc., Palo Alto, Calif.), was used as an adjuvant. The rabbit was bled by cardiac puncture three weeks after the last immunization and the serum separated.

The rabbit antiserum (anti-IrV) raised against vaccine specific antigens was reactive with each of the glycoproteins used for immunization. It immunoprecipitated metabolically labeled schistosomula and adult worm glycoproteins identical to those antigens showing a unique or enhanced immunoactivity with sera from twice-vaccinated mice, as assessed by two-dimensional SDS-PAGE analysis. The rabbit antiserum also reacted with the major surface-iodinated antigens of newly transformed schistosomula and schistosomula cultured for three to six hours in vitro. The anti-IrV antiserum immunoprecipitated six surface-labeled polypeptides of newly transformed schistosomula. The greatest reactivity was directed toward polypeptides of the following sizes: greater than 300,200,150 (a doublet), and 32–38 kDa.

EXAMPLE 2

This example demonstrates recombinant cDNA expression clones reactive with anti-IrV sera and the nucleotide sequence determined therefrom.

In order to obtain large quantities of schistosomular antigens necessary for active vaccination experiments, we have constructed an adult worm cDNA expression library in lambda-gt11 and have screened this library with the anti-IrV sera. Clones were identified which were reactive with the antiserum. Southern blots probed with radio-labeled transcripts of the cDNA inserts of each clone confirm the presence of homologous sequences of DNA in the genome of *S. mansoni*. Northern blots probed in the same manner showed that the clones hybridized to an mRAN transcript of approximately 8 kb.

The nucleotide sequence of the insert of one of these clones, termed clone IrV-5, is shown in FIG. 1a. The deduced amino acid sequence of the insert DNA is shown in FIG. 1b, line I. The DNA sequence was determined by the dideoxy-chain termination method of Sanger et al. Proceedings of the National Academy of Sciences U.S.A., vol. 74, page 5463 (1977). The 1583 basepair sequence contains one large open reading frame encoding a polypeptide of 62 kDa.

A computerized comparison of the predicted amino acid sequence shown in FIG. 1b of the IrV-5 clone with that of other sequences in the National Biomedical Research Foundation Library revealed 48% identity with the amino acid sequence of the myosin heavy chain of the nematode *C. elegans*. The similar region partially overlaps the S-1, S-2, and rod regions of *C. elegans* myosin heavy chain (residues 727 to 1256). Residues 121 through 572 of IrV-5, similar to the rod region of *C. elegans* myosin, shows the high predicted alpha-helix probability profile and a periodic seven-residue pattern with hydrophobic residues concentrated at positions 1 and 4, characteristic of alpha-helical coiled-coil proteins. These results suggest that clone IrV-5 partially encodes a schistosome myosin.

FIG. 1b, line II displays the amino acid sequence of the myosin heavy chain of *C. elegans*. Four dots between the residues of line I and line II represent identical amino acids. Two dots between the amino acid residues represent conservative amino acid substitutions, as ranked by the FASTP Program of Lipman and Pearson. Gaps introduced in the amino acid sequence to allow maximal alignment between the two sequences are indicated as -. Asterisks represent potential N-linked glycosylation sites in the sequence of IrV-5. FIG. 1c diagrammatically represents the areas of homology between the schistosome and *C. elegans* myosin molecules.

EXAMPLE 3

This example demonstrates the immunological similarity between the expression product of the clone IrV-5 and myosins of other species.

The 185 kDa fusion polypeptide consisting of schistosome sequences linked to beta-galactosidase sequences was recognized by polyclonal antibodies directed against bovine uterine smooth muscle myosin and by a monoclonal antibody against the S-2 region of the myosin heavy chain of *C. elegans*.

Antisera were raised against highly purified fusion polypeptide from clone IrV-5. The antisera were prepared in C56BL/6 mice as follows: *E. coli* CAG456 were infected with recombinant phage IrV-5, induced with isopropyl-beta-D-thiogalactopyranoside, grown for three hours and lysed. Proteins were resolved by 10% SDS-PAGE, and the IrV-5 fusion protein was purified to apparent homogeneity by electroelution. The protein was complexed to Quil A, then centrifuged to form iscoms (immunostimulatory complexes) according to the method of Morein et al., Nature, vol. 308, page 457 (1984). Mice were immunized three times subcutaneously with a total of 45 µg. Antisera against bacterial lysates infected with parental lambada-gt11 (anti-beta-galactosidase sera) were similarly prepared.

Figure 2:
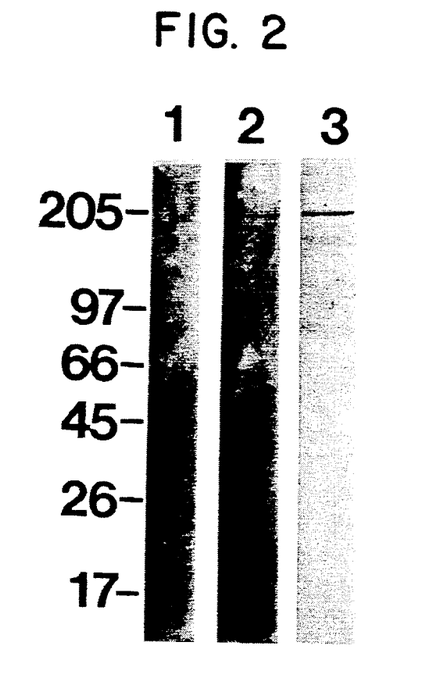
FIG. 2 shows the identification of the native protein encoded by the clone IrV-5.

The anti-fusion protein antisera recognized a signal component of 200 kDa in immunoblots of extracts from both schistosomula and adult worms. Concanavalin A affinity-purified glyucoprotein fractions from both developmental stages gave an identical result. Results are shown in FIG. 2.

Glycoproteins obtained as described in Dalton et al. Journal of Immunology, vol. 136, page 4689, 1986, from extracts of adult worms (lanes 1 and 2) and newly transformed schistosomula (lane 3) were electroblotted to nitrocellulose as described in Harn et al., Journal of Experimental Medicine, vol. 159, page 1371, 1984. Filters were probed with antiserum against beta-galactosidase (lane 1) or against IrV-5 fusion proteins (lanes 2 and 3). Bound antibody was detected by use of biotinylated anti-mouse or anti-rabbit IgG followed by avidin-conjugated horseradish peroxidase (Vector Laboratories, Burlingame, Calif.).

EXAMPLE 4

This example demonstrates the recognition of surface proteins by the anti-fusion protein antisera.

Figure 3:
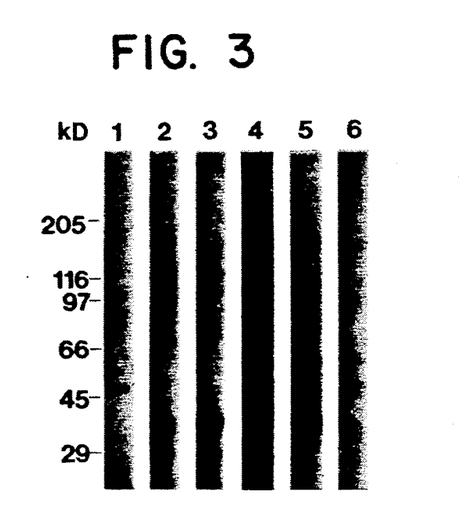
FIG. 3 shows the identification of the surface labeled polypeptides recognized by anti-fusion protein antisera.

Newly transformed schistosomula were surface-labeled with radio-iodine using the Iodo-Gen method (see Dalton et al., Journal of Immunology, vol. 139, page 2474, 1987). The labeled proteins were extracted with 1% NP 40, and immunoprecipitated as described in Dalton et al., Journal of Immunology, vol. 136, 1986, except that Sepharose CL 4B-protein A was used as the immunoadsorbant. The immunoprecipitated, labeled proteins were separated on 5%–15% SDS-PAGE, and autoradiographed.

In FIG. 3, lane 1, polypeptides were immunoprecipitated with anti-beta-galactosidase antiserum. In lane 2 sera of mice vaccinated twice with radiation-attenuated cercariae were used to precipitate the radiolabeled proteins. In lane 3 anti-fusion protein antiserum was used to precipitate the radio labeled proteins. In lane 4 monoclonal antibody 12.1.1 directed against *C. elegans* myosin was used to immunoprecipitate radiolabeled proteins. In lane 5 anti-bovine myosin antiserum was used to immunoprecipitate. In lane 6, normal rabbit serum was used to precipitate labeled proteins.

The anti-fusion protein antisera specifically immunoprecipitated a 38-kDa component from an extract of surface-labeled schistosomula. This 38 kDa component was also immunoprecipitated by antibodies against bovine myosin and *C. elegans* myosin and by sera of mice vaccinated twice with radiation-attenuated cercariae. No 38 kDa component was detected by immunoblotting, perhaps due to a low concentration of this surface polypeptide relative to total glycoproteins. (See previous Example).

EXAMPLE 5

This example demonstrates that the 38 kDa glycoprotein recognized by the anti-fusion protein antisera was the same 38 kDa molecule as that precipitated by various monoclonal antibodies described in the literature.

Sequential immunoprecipitations were carried out using a monoclonal antibody designated 128. This monoclonal antibody which is described in Dalton et al. Experimental Parasitology, vol. 63, pages 215–226 (1987) recognizes glycanic epitopes on a 38 kDa polypeptide of schistosomula. As demonstrated in FIG. 4, monoclonal antibody 128 and the anti-fusion protein antisera recognize the same component.

Figure 4:
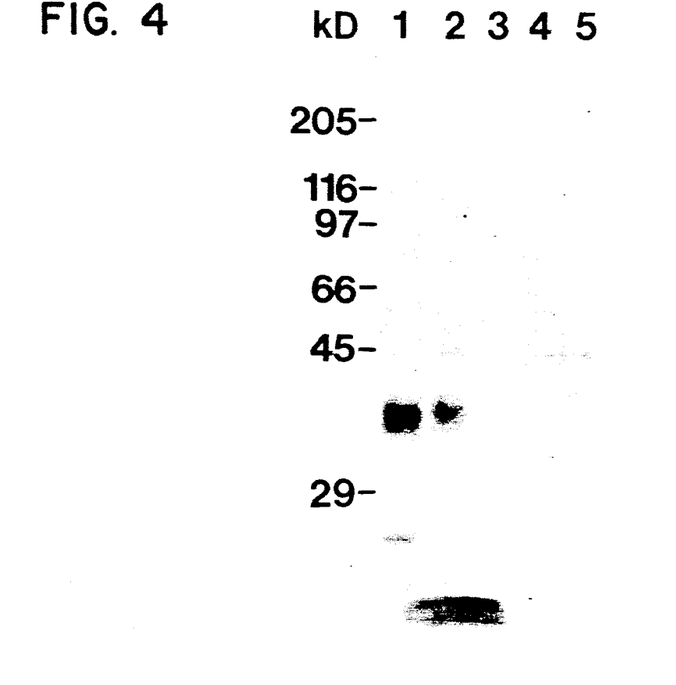
FIG. 4 shows the sequential immunoprecipitation of surface labeled polypeptides of *S. mansoni*.
Figure 5A:
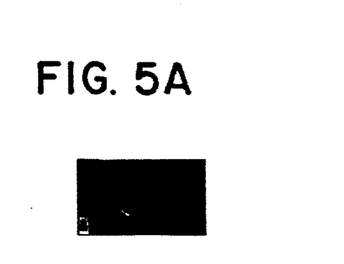
FIGS. 5A-F show surface binding of anti-fusion protein antisera to newly transformed schistosomula.
Figure 5B:
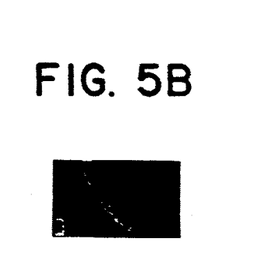
Figure 5C:
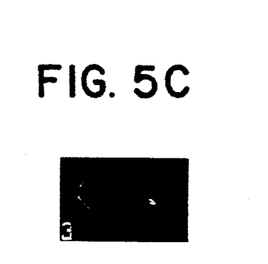
Figure 5D:
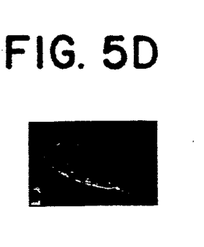
Figure 5E:
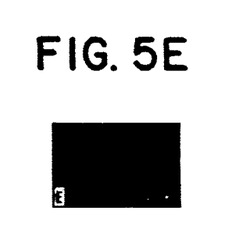
Figure 5F:
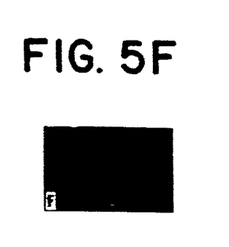

Schistosomula, surface-iodinated and extracted as above, were incubated with monoclonal antibody 128 or with normal mouse sera cross-lined to Sepharaose 4B beads. Following extensive washing the specifically bound fractions were eluted with 0.05M diethylanolamine, pH 11.5, and neutralized. Aliquots of the supernatants were then immunoprecipitated and processed as described above.

Lane 1 shows the result of a primary incubation with monoclonal antibody 128 and secondary precipitation with monoclonal antibody 128. The lane 2 shows a primary incubation with monoclonal antibody 128 and a secondary incubation with anti-fusion protein antiserum. In lanes 3 to 5 the primary incubation was with normal mouse serum. In lane 3 the secondary precipitation was with monoclonal antibody 128. In lane 4 the secondary precipitation was with anti-fusion protein. And in lane 5 the secondary precipitation was with normal mouse serum. These experiments demonstrate that monoclonal antibody 128 and the anti-fusion protein antiserum recognize the same component.

EXAMPLE 6

This example demonstrates that anti-fusion protein antiserum binds to the surface of newly transformed schistosomula.

Live schistosomula were incubated for one hour on ice with monoclonal antibody 128 (FIG. 5 panels A and B); anti-fusion protein antiserum (panels C and D); and anti-beta-galactosidase antiserum (panels E and F). Bound antibody was detected using affinity purified rabbit anti-mouse IgG obtained from Jackson Immuno Research, followed by Rhodamine-conjugated protein A (Cappel Scientific Division, Cooper Biomedical Inc., Malvern, Pa.) panels A, C and E); and phase contrast views of the schistosomula are shown in panels B, D, and F. Surface integrity of schistosomula during the course of the immunofluorescence assays was verified by use of diamidinophenylindole, a flurochrome specifically taken up by damaged schistosomula.

Both the anti-fusion protein antiserum and monoclonal antibody 128 showed strong binding to the surface of live, newly transformed schistosomula. However, no surface binding was detected using the antibodies against bovine or *C. elegans* myosin or antiserum raised against purified beta-galactosidase. Thus, the anti-fusion protein antiserum defines epitopes exposed on the surface of live schistosomula, and these epitopes are not recognized by antibodies against myosin derived from other species.

EXAMPLE 7

This example demonstrates the immunoprophylactic potential of the IrV-5 fusion protein.

Groups of mice (8 mice per group) were immunized with 5 to 20 μg of purified IrV-5 fusion protein, administered either in the form of immuno-stimulatory complexes (Iscoms) using Quil A or mixed with *Cornynebacterium parvum* or Freund's adjuvant. The mice were immunized subcutaneously on days 0, 14 and 28. On day 38 the mice were challenged with 125 cercariae and on day 94 mice were perfused and the number of worms in the perfusate was counted. Table 1 shows the results obtained. The reduction in worm burden particularly with iscoms and *C. parvum* is notable.

TABLE I

| VACCINATION TRIAL WITH IrV-5 FUSION PROTEIN | | | |
|---|---|---|---|
| Group | +/− S.D. | Worm Recovery % Reduction | p value |
| Control | 40.5 ± 5.0 | 4.6 | Not significant |
| C. parvum only | 38.6 ± 8.5 | | |
| IrV-5/Iscoms | 25.1 ± 8.4 | 36.0 | 0.002 |
| gt11/Iscoms | 39.2 ± 2.8 | | |
| IrV-5/C. parvum | 24.2 ± 2.0 | 35.3 | 0.003 |
| gt11/C. parvum | 37.4 ± 6.2 | | |
| IrV-5/Freund's | 28.1 ± 3.4 | 18.3 | 0.038 |
| gt11/Freund's | 34.4 ± 6.7 | | |

EXAMPLE 8

This example demonstrates the isolation of a polypeptide of the present invention substantially free of other proteins.

The insert from the recombinant IrV-5 clone in lambda gt11 (rIrV-5) was subcloned into the modified PGX-2T vector (Smith and Johnson, Gene, vol. 67, pp. 31–40, 1988) and transfected into *E. coli* HB101 cells. The fusion protein produced by this vector consists of a glutathione-S-transferase (GST), a thrombin cleavage site and rIrV-5. The fusion protein was applied to a glutathione-agarose affinity column to remove all proteins which do not bind to glutathione. The fusion protein so purified was then subjected to cleavage by thrombin. The cleaved protein mixture was then applied to a glutathione-agarose column to remove the GST; the rIrV-5 polypeptide was collected from the column run-through fraction.

EXAMPLE 9

This example demonstrates the preparation of rIrV-5/proteosomes.

Outer membrane proteins (OMP) from group B serotype meningococci were prepared according to Zollinger et al., J. Clin. Investig., vol. 63, pp. 836–848, 1979.

Proteosomes were prepared according to the method of Reugg, *J. Imm. Methods*, vol. 135, pp. 101–109, 1990. The ratio of rIrV-5 to OMP in the proteosomes was varied and the efficacy of the resulting proteosomes as vaccines were tested in mice. Optimum immunoprophylactic potency was observed at a rIrV-5 to OMP ratio of 2:1 (w/w). See Table II.

EXAMPLE 10

This example demonstrates the relative efficacies of a number of different proteosome vaccines.

Proteosomes were prepared according to the method of Ruegg et al., supra. Proteosomes containing the IrV-5 beta-galactosidase fusion protein were compared to proteosomes containing proteins produced by the lambda gt11 vector alone, as well as those containing the cleaved rIrV-5 polypeptide discribed above and synthetic peptides containing sequences from the immunodominant $(NANP)_n$ tandem repeat region of *Plasmodium falciparum*, as described in Ruegg et al., supra. A ratio of 1:1 test protein to OMP was used, and 10 ug of test protein was used per vaccine. The cleaved rIrV-5 polypeptide performed better than twice as well as the IrV-5 beta-galactosidase fusion. See Table III.

TABLE II

IrV-5/OMP-PROTEOSOME VACCINATION

| Groups | No. of Worms | % Reduction | p value |
|---|---|---|---|
| Control-PBS | 69.0 ± 18.6 | — | — |
| 10 ug IrV-5 | 26.2 ± 10.2 | 62.0 | 0.0020 |
| 10 ug IrV-5 (20 ug OMP) | 25.2 ± 13.4 | 63.5 | 0.0027 |
| 5 ug IrV-5 (10 ug OMP) | 39.8 ± 26.1 | 42.3 | 0.0761 |
| 10 ug IrV-5 (5 ug OMP) | 19.2 ± 15.3 | 72.2 | 0.0017 |
| 20 ug IrV-5 (10 ug OMP) | 42.4 ± 15.3 | 38.6 | 0.0384 |
| 10 ug IrV-5 (1.2 ug OMP) | 33.8 ± 8.3 | 51.0 | 0.0048 |
| 80 ug IrV-5 (10 ug OMP) | 11.8 ± 13.7 | 82.9 | 0.0005 |

TABLE III

IrV-5/OMP-Proteosome Vaccination

| Groups | No. of Worms | % Reduction | p. value |
|---|---|---|---|
| IrV-5/Proteosome* | 41.7 ± 32.8 | 31.9 | 0.1233 |
| λgt11/Proteosome | 61.2 ± 8.8 | — | — |
| cIrV-5/Proteosome** | 14.6 ± 22.0 | 75.3 | 0.0005 |
| malaria/Proteosome | 59.0 ± 19.0 | — | — |

*IrV-5 beta-galactosidase fusion protein
**cleaved IrV-5

I claim:

1. A cDNA molecule which codes for a polypeptide consisting essentially of the amino acid sequence of FIG. 1, B1, said polypeptide being able to bind to antibodies which bind to protein epitopes but not glycanic epitopes expressed on the surface of live schistosomula of *S. mansoni*, said protein epitopes being common to a 200 kDA and a 38 kDa glycoprotein of *S. mansoni*.

2. A vaccine comprising:
   a polypeptide consisting essentially of the amino acid sequence of FIG. 1, B1, said polypeptide being able to bind to antibodies which bind to protein epitopes but not glycanic epitopes expressed on the surface of live schistosomula of *S. mansoni*, said protein epitopes being common to a 200 kDa and a 38 kDa glycoprotein of *S. mansoni*; and
   an immune adjuvant.

3. The vaccine of claim 2 wherein the immune adjuvant is selected from the group consisting of: Quil A, and bacterial outer membrane proteins.

4. The vaccine of claim 2 wherein the vaccine is in the form of iscoms or proteosomes.

5. A method of protecting a mammal against schistosomiasis comprising:
   immunizing a mammal with a composition comprising a polypeptide consisting essentially of the amino acid sequence of FIG. 1, B1, said polypeptide being able to bind to antibodies which bind to protein epitopes but not glycanic epitopes expressed on the surface of live schistosomula of *S. mansoni*, said protein epitopes being common to a 200 kDa and a 38 kDa glycoprotein of *S. mansoni*.

6. The method of claim 5 wherein the step of immunizing is by subcutaneous administration.

* * * * *